(12) United States Patent
Gitlin et al.

(10) Patent No.: US 8,416,342 B1
(45) Date of Patent: Apr. 9, 2013

(54) IMPLANTABLE IMAGING DEVICE (75) Inventors: Richard Gitlin, Tampa, FL (US); Craig Lusk, Lutz, FL (US); Shekhar Bhansali, Tampa, FL (US); Alexander Rosemurgy, Tampa, FL (US)

(73) Assignee: University of South Florida, Tampa, FL (US)

( * ) Notice: Subject to any disclaimer, the term of this patent is extended or adjusted under 35 U.S.C. 154(b) by 299 days.

(21) Appl. No.: 12/702,704

(22) Filed: Feb. 9, 2010

Related U.S. Application Data

(60) Provisional application No. 61/150,889, filed on Feb. 9, 2009.

(51) Int. Cl.
*H04N 5/225* (2006.01)
*H04N 3/14* (2006.01)

(52) U.S. Cl. ............... 348/373; 348/294; 359/830

(58) Field of Classification Search ........... 348/373, 348/294, E5.026
See application file for complete search history.

(56) References Cited

U.S. PATENT DOCUMENTS

| | | | |
|---|---|---|---|
| 5,604,531 A | 2/1997 | Iddan et al. | |
| 6,402,689 B1 | 6/2002 | Scarantino et al. | |
| 6,546,272 B1 | 4/2003 | MacKinnon et al. | |
| 7,009,634 B2 | 3/2006 | Iddan et al. | |
| 7,214,182 B2 | 5/2007 | Shimizu et al. | |
| 7,229,456 B2 * | 6/2007 | Lang et al. | 606/170 |
| 7,338,495 B2 * | 3/2008 | Adams | 606/79 |
| 8,114,097 B2 * | 2/2012 | Brock et al. | 606/130 |
| 8,182,418 B2 * | 5/2012 | Durant et al. | 600/142 |
| 2007/0255098 A1 | 11/2007 | Wang et al. | |
| 2007/0270651 A1 | 11/2007 | Gilad et al. | |
| 2008/0100934 A1 * | 5/2008 | Webster et al. | 359/830 |
| 2010/0081875 A1 * | 4/2010 | Fowler et al. | 600/114 |
| 2010/0142061 A1 * | 6/2010 | Choi et al. | 359/793 |

OTHER PUBLICATIONS

Hu et al., Insertable Surgical Imaging Device with Pan, Tilt, Zoom, and Lighting, IEEE International Conference on Robotics and Automation, May 2008.
Hu et al., Insertable Stereoscopic 3D Surgical Imaging Device with Pan and Tilt, IEEE International Conference on Biomedical Robotics and Biomechatronics (BioRob 2008).
Hu et al., In-Vivo Pan/Tilt Endoscope with Integrated Light Source, IEEE/RSJ International Conference on Intelligent Robots and Systems, 2007, San Diego.

* cited by examiner

*Primary Examiner* — Hung Lam
(74) *Attorney, Agent, or Firm* — Nilay J. Choksi; Wanhua Zhao; Smith & Hopen, P.A.

(57) ABSTRACT

An imaging device for in vivo medical applications that enables minimally invasive surgical procedures. The imaging device includes an elongated frame having a base, a module housing, and a helical member interposed between the base and module housing. The imaging device further includes an actuation unit positioned within the frame that engages the module housing causing the frame to bend at the helical member. The module housing includes an imaging module and may include other modules including tools used for laparoscopic surgery.

24 Claims, 8 Drawing Sheets

IMPLANTABLE IMAGING DEVICE

CROSS REFERENCE TO RELATED APPLICATIONS

This application claims priority to currently pending U.S. Provisional Patent Application No. 61/150,889, entitled "Implantable and Controllable Camera", filed Feb. 9, 2009, which is hereby incorporated by reference.

FIELD OF INVENTION

This invention relates to a device for minimally invasive surgical procedures; more specifically, an implantable and controllable imaging device appropriate for in vivo medical applications.

BACKGROUND

As minimally invasive surgical (MIS) procedures become increasing sophisticated, new functions will be needed to realize successful surgical outcomes. For example, conventional laparoscopy places a limit on the number of devices that can be inserted in the body. In addition, these devices have limited positioning capabilities and may compete or interfere with the preferred motion or position of another instrument.

SUMMARY

The present invention includes an implantable imaging device for use in minimally invasive medical procedures that can be wirelessly controlled and can wirelessly transmit images. This frees the ports that would normally be used by a laparoscope, enabling surgeons to use additional tools or to use the current devices with more mobility.

The imaging device includes an elongated frame having a base, a module housing, and a helical portion interposed between the base and the module housing. The imaging device further includes an actuation unit positioned within the frame that engages the module housing causing the frame to bend at the helical portion. The helical portion may be a single or double helix structure.

In an embodiment, the module housing further includes an imaging module and may include other modules including tools used for laparoscopic surgery. The imaging module may include zoom, autofocus, and/or image stabilization features. The imaging module may also include a window positioned on the end of the module housing opposite the helical portion.

The imaging device may further include a lens system positioned within the module housing to focus images coming into the imaging module onto an image sensor. The imaging device may also include an additional lens system that guides light from light sources in the imaging module out of the imaging module.

The frame may be sized to fit into a trocar package. In addition, a needle may be positioned on the end of the base. The housing module may be introduced into the body cavity separately from the remainder of the frame and then assembled in vivo.

The imaging device may include a control unit in communication with the actuation unit. There may also be a wireless communication device in communication with the control unit. Additionally, the imaging device may include a light source. The light source may be a controlled light source having multiple wavelengths and variable intensity control.

In another embodiment, the base may include a base support platform and the module housing may include a housing support platform. The actuation unit is affixed to the base at the base support platform and positioned to engage the module housing at the housing support platform. The imaging device may also include a rod attaching the base and the housing support platform.

In an additional embodiment, the actuation unit may include a casing that has an axial passage and a motor positioned at least partially in the axial passage. A shaft extends from the motor and is positioned to engage the module housing, causing the frame to bend at the helical portion.

Alternatively, the actuation unit may include a housing support platform located inside the module housing, a casing with an axial passage, and a motor positioned at least partially in the axial passage. A shaft extends from the motor and is positioned to engage said housing support platform, causing the frame to bend at the helical portion.

As another alternative, the actuation unit may include a motor with a shaft and a piston. The piston is positioned to engage the shaft and the module housing such that linear movement of said shaft causes linear movement of said piston. The actuation unit may also include a housing support platform positioned within the module housing. The piston would then engage the module housing at the housing support platform.

Additionally, the actuation unit may include a motor with a shaft, which has an arm. A tether connects the arm and the module housing. Movement of the arm causes the tether to wrap around the shaft, which pulls on the module housing. As the module housing is pulled towards the base it causes the frame to bend at the helical portion. The actuation unit may also include a housing support platform positioned within the module housing. The tether would then connect to the module housing at the housing support platform.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

In the following detailed description of the preferred embodiments, reference is made to the accompanying drawings, which form a part hereof, and within which are shown by way of illustration specific embodiments by which the invention may be practiced. It is to be understood that other embodiments may be utilized and structural changes may be made without departing from the scope of the invention.

The present invention includes an implantable, controllable imaging device for in vivo medical applications. The imaging device enables minimally invasive surgical procedures. Example applications include procedures in the ventral cavity. The imaging device may also provide the ability to film the progress of internal wound healing over a period of days or weeks, allowing for better monitoring of surgical outcomes.

Figure 1:
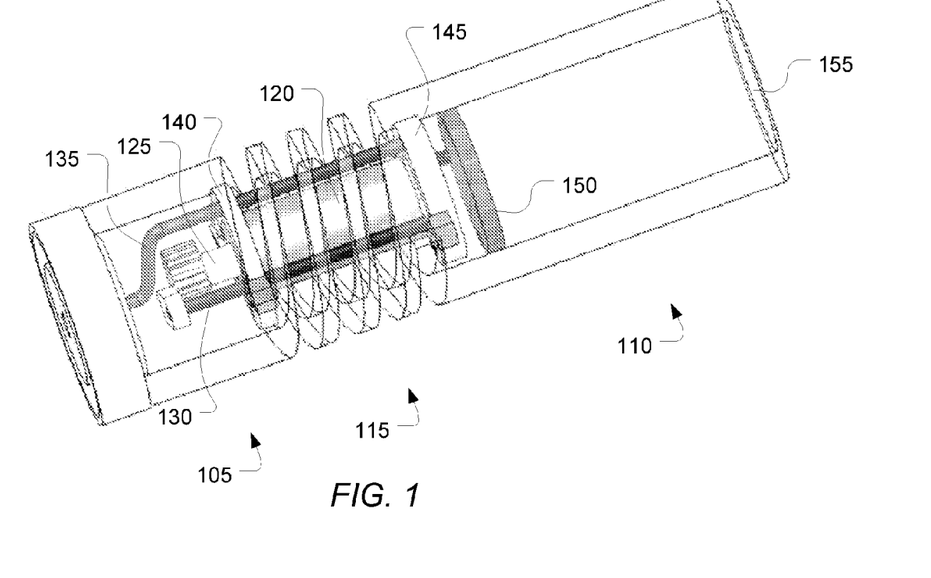
FIG. 1 is a diagram of an imaging device with its motor located in the helical portion of the frame according to an embodiment of the present invention.

An embodiment of the imaging device is shown in FIG. 1. In this embodiment, the imaging device includes a frame and an actuation unit. The frame includes base 105 and module housing 110 connected by helical portion 115. Module housing 110 includes power source 150 and may contain a laparoscopic surgery tool, such as an imaging module, a light source, or temperature sensor. Module housing 110 may also include window 155, which would be needed for tools such as an imaging module or a light source. A flexible covering may also be included over helical portion.

Figure 2:
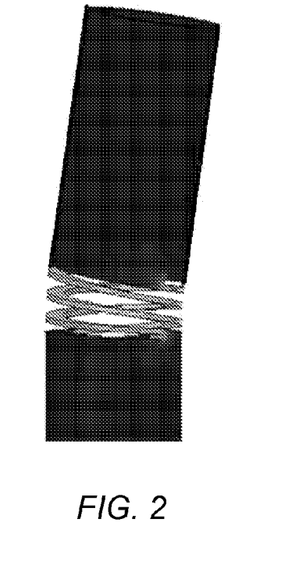
FIG. 2 is a diagram the frame of an imaging device showing the frame's ability to bend according to an embodiment of the present invention.

Helical portion 115 may be a single helix structure or a double helix structure. Helical portion 115 allows the frame to bend responsive to movement caused by the actuation unit. The actuation unit, in this embodiment, includes motor 120, shaft 125, piston 130, rod 135, base support platform 140, and housing support platform 145. Motor 120 is secured in its position within helical portion by housing support platform 145 and base support platform 140. Rod 135 connects base 105 to housing support platform. As shaft 125 extends from motor 120, piston 130 pulls on housing support platform 145 causing helical portion 115 to compress on one side while rod 135 works to prevent compression on the opposing side of helical portion 115. This movement causes the imaging device's frame to bend as shown in FIG. 2. As shaft 125 retracts, helical portion 115 is allowed to expand and return imaging device to its un-bent position. If shaft 125 continues to retract, the tension in helical portion 115 will cause helical portion 115 to continue to expand on one side, while rod 135 works to prevent expansion on the opposing side. This movement causes the imaging device's frame to bend in the opposite direction.

Figure 3:
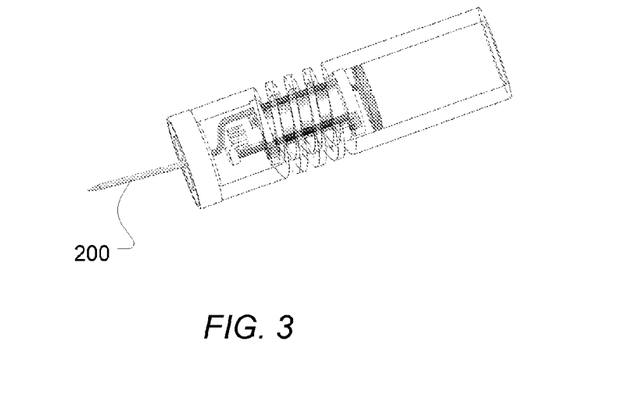
FIG. 3 is a diagram of a transdermal needle attached to an imaging device according to an embodiment of the present invention.

The imaging device is sized to fit in a trocar package and may include transdermal needle 200, as illustrated in FIG. 3. The module housing may be injected into the body cavity separately from the remainder of the device and then assembled in vivo.

Figure 4A:
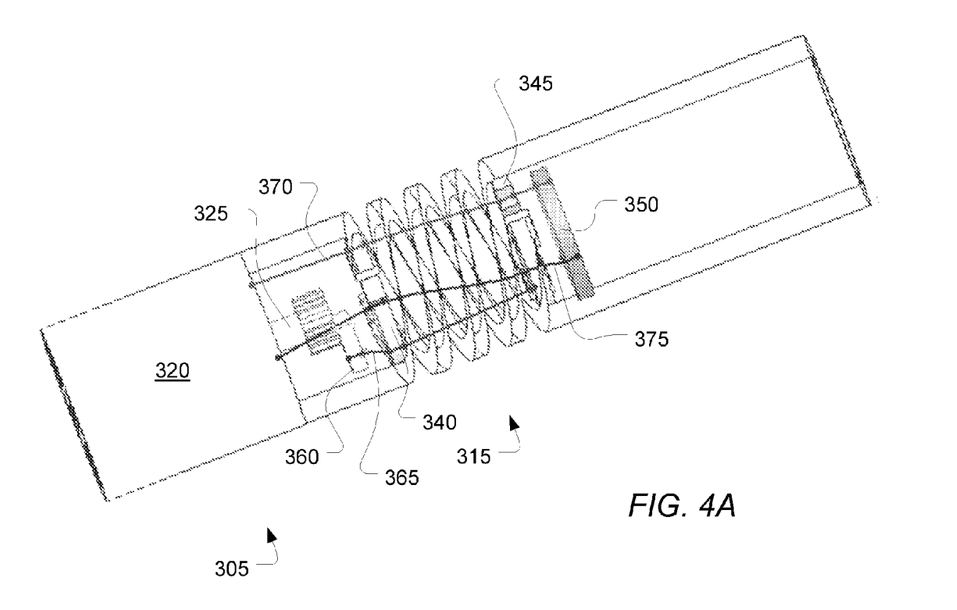
FIG. 4A is a diagram of an imaging device with its motor located in the base portion of the frame in its unbent position according to an embodiment of the present invention.
Figure 4B:
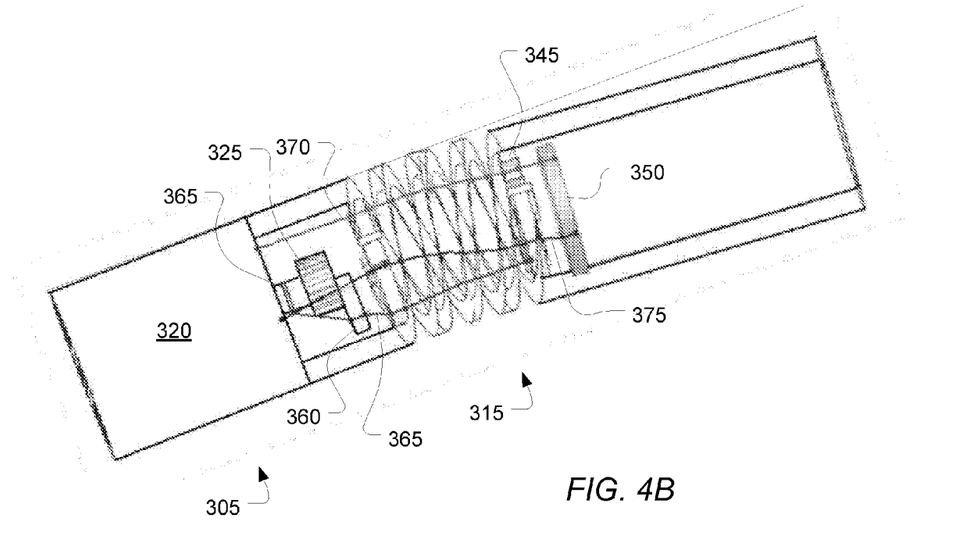
FIG. 4B is a diagram of an imaging device with its motor located in the base portion of the frame in a bent position according to an embodiment of the present invention.
Figure 4C:
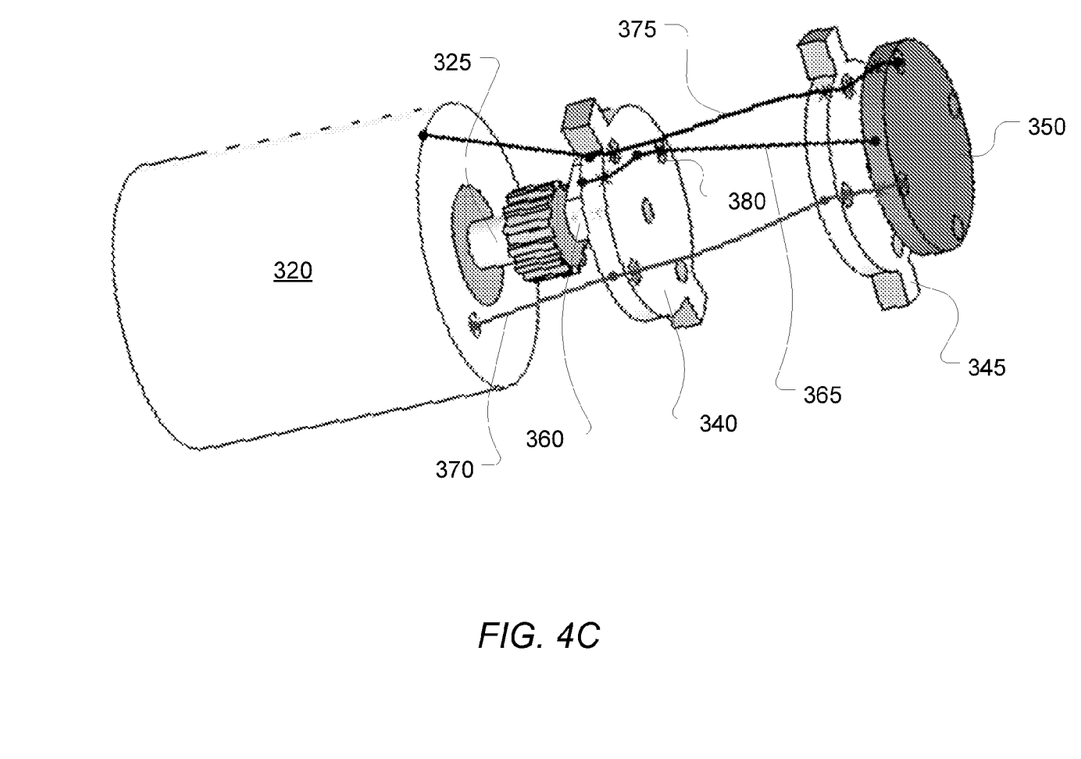
FIG. 4C is a diagram of the actuation unit of the imaging device shown in FIGS. 4A and 4B according to an embodiment of the present invention.

In another embodiment, as illustrated in FIGS. 4A, 4B, and 4C, the actuation unit includes motor 320 with shaft 325, shaft arm 360, base support platform 340, housing support platform 345, and tether 365. Tether 365 is connected to shaft arm 360, threaded through aperture 380 (FIG. 4C) in base support platform 340, and connected to housing support platform 345. As motor 320 rotates shaft 325 and shaft arm 360, tether 365 wraps around shaft 325, as shown in FIG. 4B. As tether 365 wraps around shaft 325, it pulls on housing support platform 345 causing helical portion 315 to compress on one side. This movement causes the imaging device's frame to bend as shown in FIG. 4B. As motor 320 turns shaft 325 and shaft arm 360 in the opposite direction, tether 365 unwraps from around shaft 325 allowing helical portion 315 to expand and return imaging device to its unbent position.

A rod (not shown) may also be included to provide movement (bending) in the opposite direction, similar to the embodiment shown in FIG. 1. Here, the rod would connect base 305, such as at motor 320, to housing support platform 345. The frame would be in an unbent position when tether 365 was wrapped around shaft 325 a predetermined number of times. As motor 320 turned shaft 325 in a first direction, tether would further wrap around shaft 325, causing the frame to bend as described previously and shown in FIG. 4B. As motor 320 turned in the opposite direction, tether 365 would unwrap. Once the number of times tether 365 was wrapped around shaft 325 was less than the predetermined number of times required to keep frame in its unbent position, the frame would begin to bend in the opposite direction.

FIGS. 4A, 4B, and 4C also show the placement of power lines 370 and 375 connecting power 350 to motor 320.

Figure 5:
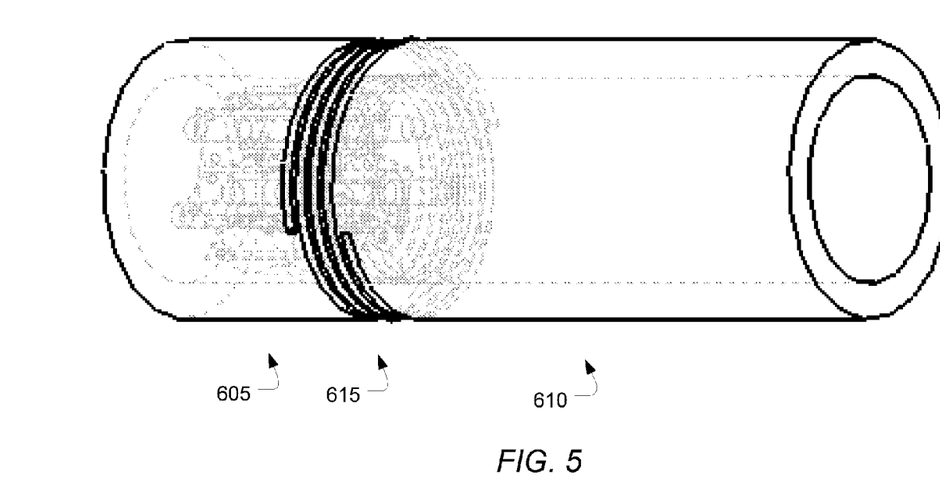
FIG. 5 is a diagram of an imaging device with an actuation unit that contains a casing and multiple motors according to an embodiment of the present invention.
Figure 6:
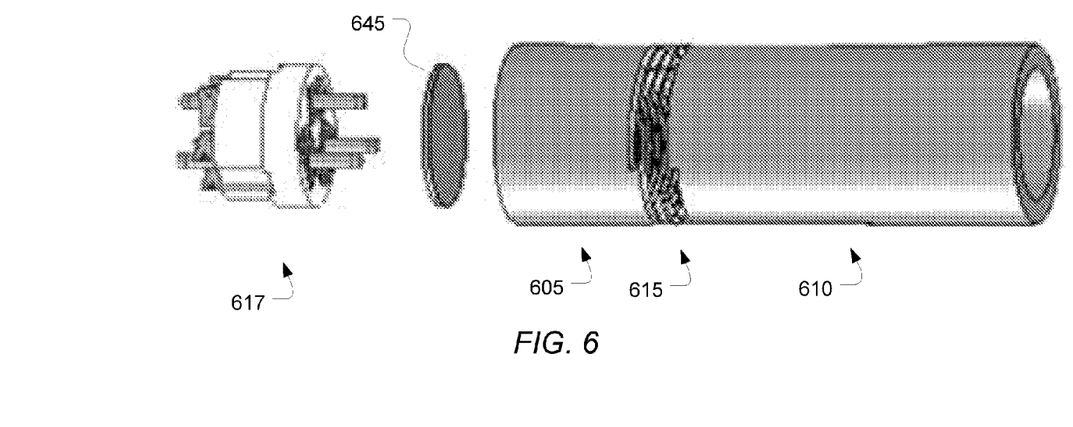
FIG. 6 is an exploded view of the imaging device shown in FIG. 5 according to an embodiment of the present invention.
Figure 7A:
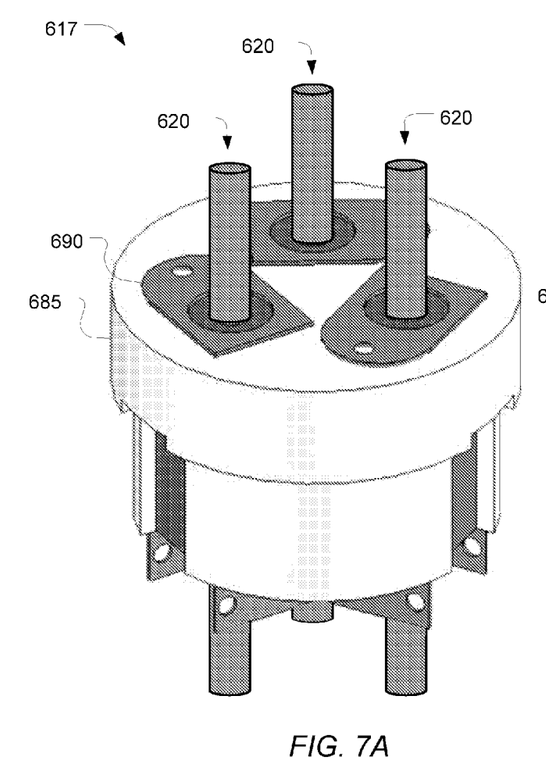
FIG. 7A is a diagram of the actuation unit of the imaging device shown in FIGS. 5 and 6 according to an embodiment of the present invention.
Figure 7B:
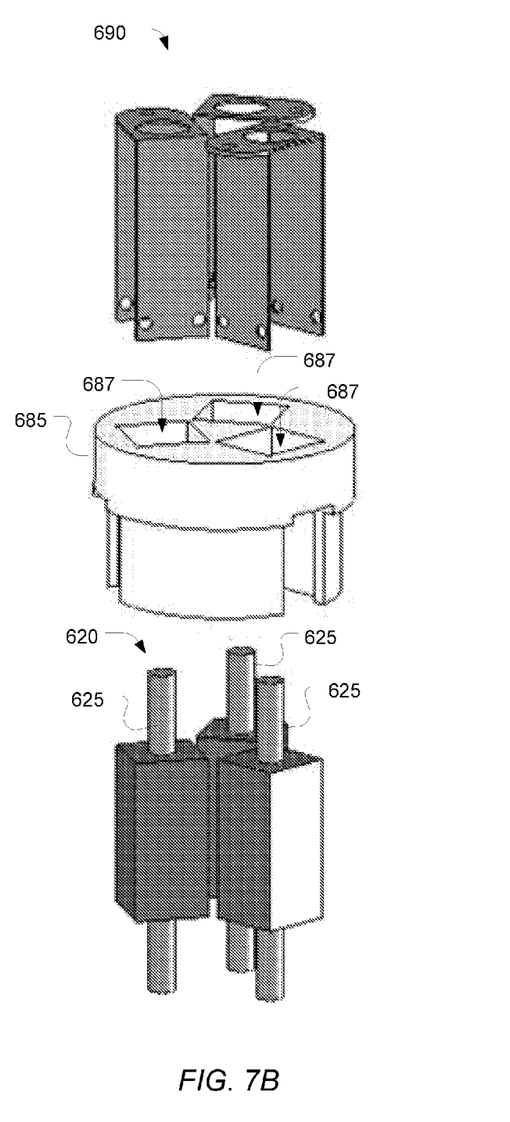
FIG. 7B is an exploded view of the actuation unit shown in FIG. 7A according to an embodiment of the present invention.
Figure 8:
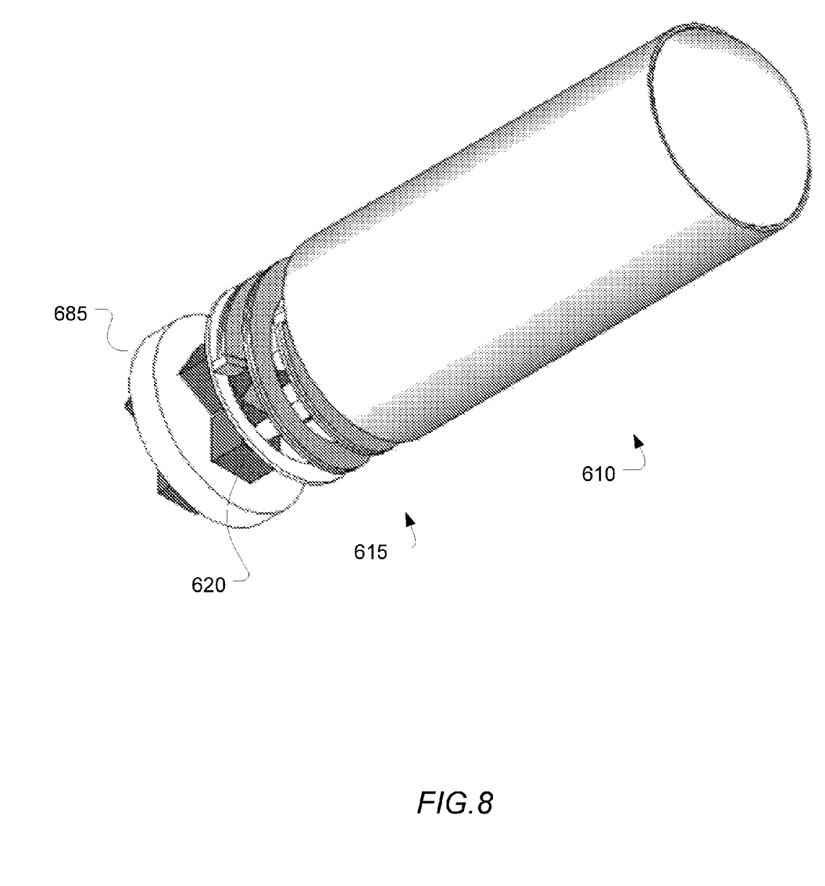
FIG. 8 is a diagram of a portion of an imaging device with an actuation unit that contains multiple motors and a modified casing according to an embodiment of the present invention.

In another embodiment, as shown in FIGS. 5 and 6, the actuation unit includes multiple motors. FIG. 5 shows the actuation unit positioned within the frame of the imaging device. FIG. 6 is an exploded view showing actuation unit 617 and housing support platform 645 outside of the frame. A more detailed view of actuation unit 617 is shown in FIG. 7A and an exploded view of actuation unit 617 is shown in FIG. 7B. As illustrated in FIGS. 7A and 7B, the actuation unit includes motors 620, each having shafts 625, casing 685, and sleeves 690. Casing 685 secures motors 620 in place within the frame and provides spacing of motors 620. Casing may be fitted within base 605 or may extend at least partially into helical portion 615. Sleeves 690 fit in passages 687 of casing 685 and are used to secure motors 620 to casing 685. Shafts 625 extend through helical portion 615 and engage housing support platform 645, which is secured to housing module 610. Movement (or bending) in this embodiment is caused when one or more of shafts 625 is extended and/or retracted from motors 620. Similar embodiment may be implemented with any number of motors/shafts. Casing 685 may also be shaped as shown in FIG. 8.

The imaging device is operated by control signals and may be tele-operable. The control signals may be optical, electrical, or magnetic. One function of these control signals is to control the depth and field of view of the imaging device. Such control signals and any other data transmitted or received by the imaging device may be transmitted/received via a wired or wireless connection.

Figure 9:
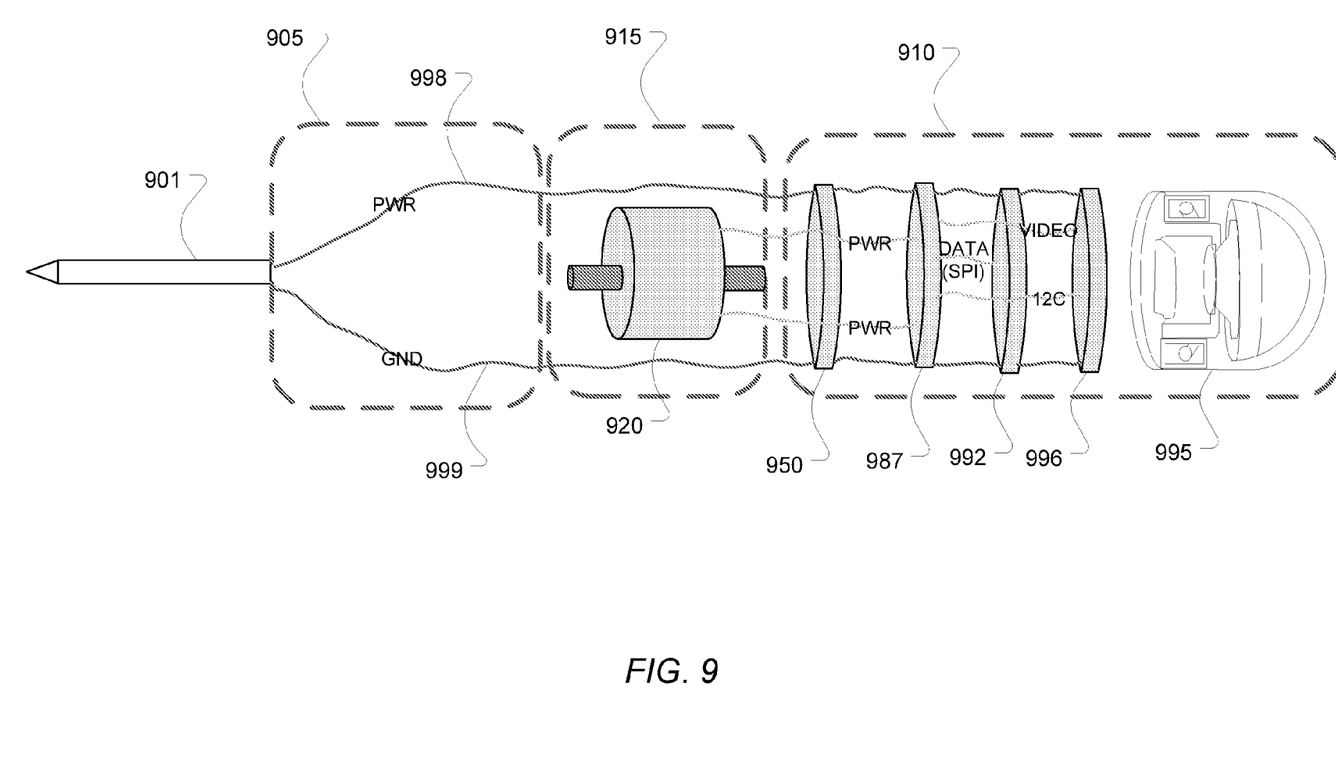
FIG. 9 is a diagram of the internal circuitry of an imaging device according to an embodiment of the present invention.
Figure 10A:
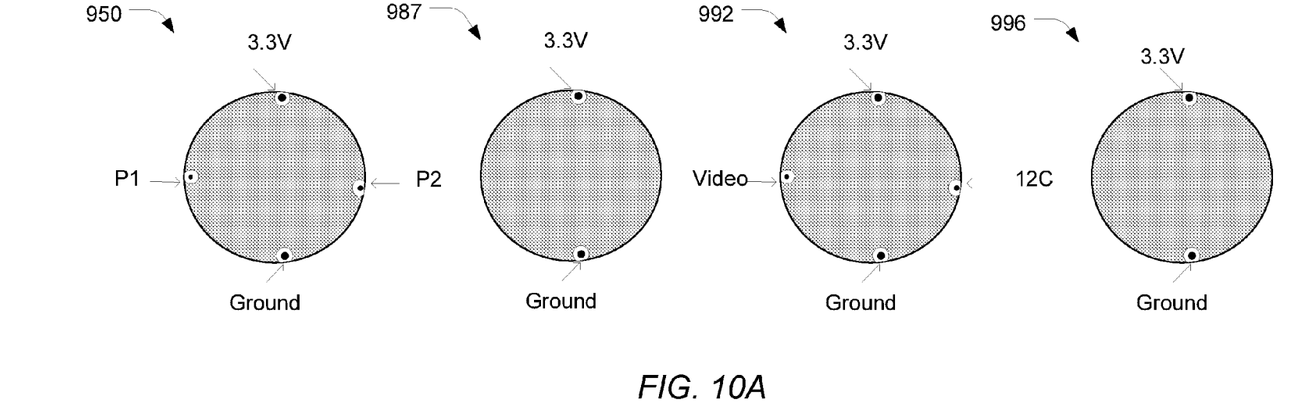
FIG. 10A is a diagram of an exemplary chip set used in the circuitry of an imaging device according to an embodiment of the present invention.
Figure 10B:
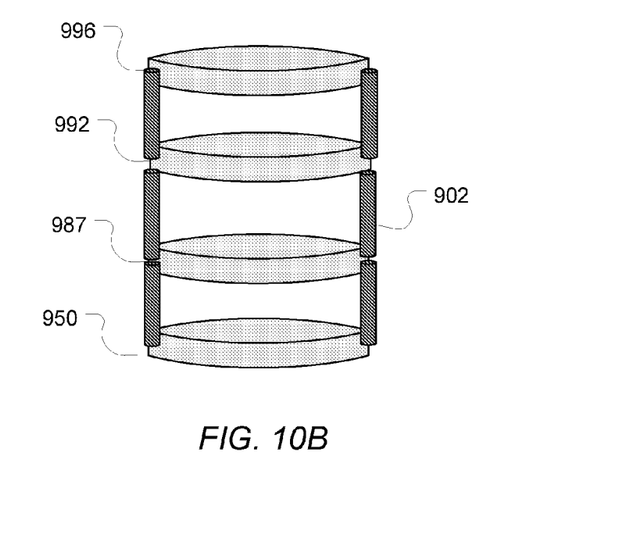
FIG. 10B is a diagram of the exemplary chip set of FIG. 10A shown stacked using multiple separators according to an embodiment of the present invention.

As shown in FIG. 9, in an embodiment, imaging device further includes imaging module 995. Imaging module 995 is connected to imaging control 996. Also included are wireless communication device 992, controller 987, and power 950. Controller 987 controls the movement of the imaging device by directing the movement of motor 920. Controller 987 is also in communication with imaging control 996 and wireless communication device 992. Wireless communication device 992 transmits images captured by imaging device 995 to a remote receiving station and receives control signals from an external control unit, which it then transmits to controller 987. Wireless communication device 992 may also be used for any other communication needed between imaging device and the control unit or other external system, such as a display system. Wireless communication device 992 may also be used for communication with other wirelessly enabled implantable devices. FIG. 10A shows top view of exemplary chip set used as power 950, controller 987, wireless communication device 992, and imaging control 996. FIG. 10B shows the chips as they would be stacked using separators 902 in module housing 910.

In addition, the imaging device may have capabilities for pan and zoom, autofocus, and/or image stabilization, which may be built into imaging module 995 or module housing 910. The imaging device may also include one or more light sources, which also may be incorporated into module housing 910 or imaging module 995. The light source may be a controlled light source having multiple wavelengths and intensity control.

The module housing may also include a lens system that focuses images into the imaging module and onto an image sensor and a lens system guiding light from light sources in the imaging module out of the imaging module, thereby minimizing deterioration of the image caused by internal reflections of light from the light sources, which are illuminating the items being viewed.

The imaging device has minimal, or no, physical connections to a patient's exterior. Example connections include a small power cord capable of being threaded using a needle adapter and a release mechanism allowing for removal of the imaging device at the point of insertion. FIG. 9 illustrates the placement of power cord 998 and ground cord 999 through the imaging device to needle 901. The imaging device may also be battery powered and, therefore, not requiring a power cord.

The imaging device may also include a propulsion system. The propulsion system allows the imaging device to move about the body cavity without the aid of a tether. The bendable frame and the actuation unit aid in orienting the imaging device inside the body cavity. The actuation of the frame may also be via shape memory effects, piezo-electric effects, electrical or magnetic actuators, or a similar method or device.

In another embodiment, two or more imaging devices are provided. The imaging devices are used, along with imaging software, to provide coordinated motion which allows for sectored views, panoramic views, electronic zoom, feature tracking (examples include tracking a specific organ or portion of an organ, or a surgical tool) or the creation of holograms (three-dimensional views) that may be viewed on displays and/or projected onto the skin of the patient.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall there between.

What is claimed is:

1. An imaging device comprising:
   an elongated frame having a base, a module housing, and a helical portion interposed between said base and said module housing;
   an actuation unit positioned within said frame, attached to said base and positioned to engage said module housing;
   a casing positioned within said bases and attached to said base, said casing having three axial passages there through, said passages spaced about equally apart from each other and about equidistant from the axial center of said casing; and
   three motors, one positioned at least partially within each said axial passage, said three motors each having a shaft extending there from, each said shaft positioned to engage said module housing.

2. The imaging device of claim 1, further comprising:
   a base support platform positioned within and secured to said base;
   a housing support platform positioned within and secured to said module housing; and
   said actuation unit affixed to said base at said base support platform and positioned to engage said module housing at said housing support platform.

3. The imaging device of claim 2, further comprising:
   a rod attached to said base and to said housing support platform.

4. The imaging device of claim 1, wherein said actuation unit comprises:
   a housing support platform positioned within and secured to said module housing; and
   a casing positioned within said base and attached to said base, said casing having an axial passage there through; and
   a motor positioned at least partially within said axial passage having a shaft extending there from, said shaft positioned to engage said housing support platform.

5. The imaging device of claim 1, wherein said actuation unit comprises:
   a housing support platform positioned within and secured to said module housing, said shaft of said three motors positioned to engage said housing support platform.

6. The imaging device of claim 1, wherein said actuation unit comprises:
   a housing support platform positioned within and secured to said module housing;
   a motor having a shaft, said shaft having an arm; and
   a tether connected at a first end to said arm and at a second end to said housing support platform.

7. The imaging device of claim 1, wherein said actuation unit comprises:
   a motor having a shaft, said shaft having an arm; and
   a tether connected at a first end to said arm and at a second end to said module housing.

8. The imaging device of claim 1, wherein said actuation unit comprises:
   a piston positioned to engage the shaft and said module housing such that linear movement of said shaft causes linear movement of said piston.

9. The imaging device of claim 1, wherein said actuation unit comprises:
   a housing support platform positioned within and secured to said module housing; and
   a piston positioned to engage the shaft and said housing support platform such that linear movement of said shaft causes linear movement of said piston.

10. The imaging device of claim 1, further comprising:
an imaging module positioned within the module housing.

11. The imaging device of claim 10, wherein said imaging device further comprises a zoom.

12. The imaging device of claim 10, wherein said imaging device further comprises an autofocus.

13. The imaging device of claim 10, wherein said imaging device further comprises image stabilization.

14. The imaging device of claim 1, further comprising:
a window positioned on the end of the module housing opposite the helical portion.

15. The imaging device of claim 1, further comprising:
a needle positioned on the end of the base opposite the helical portion.

16. The imaging device of claim 1, further comprising:
a control unit in communication with the actuation unit.

17. The imaging device of claim 16, further comprising:
a wireless communication device positioned within the module housing and in communication with the control unit.

18. The imaging device of claim 1, wherein said helical portion comprises a double helix structure.

19. The imaging device of claim 1, further comprising:
a light source positioned in said module housing.

20. The imaging device of claim 19, wherein said light source is a controlled light source having multiple wavelengths.

21. The imaging device of claim 20, wherein said controlled light source includes variable intensity control.

22. The imaging device of claim 1, wherein said frame is sized to fit into a trocar package.

23. The imaging device of claim 1, wherein said frame is cylindrical in shape.

24. The imaging device of claim 1, further comprising:
a lens system positioned within the module housing.

* * * * *